US00PP33790P3

(12) United States Plant Patent
Post

(10) Patent No.: US PP33,790 P3
(45) Date of Patent: Dec. 28, 2021

(54) ***CHRYSANTHEMUM* PLANT NAMED 'DLFPASC7'**

(50) Latin Name: ***Chrysanthemum* X *morifolium***
Varietal Denomination: DLFPASC7

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/170,561

(22) Filed: Feb. 8, 2021

(65) Prior Publication Data

US 2021/0251121 P1 Aug. 12, 2021

Related U.S. Application Data

(60) Provisional application No. 62/995,750, filed on Feb. 12, 2020.

(51) Int. Cl.
*A01H 6/14* (2018.01)
*A01H 5/02* (2018.01)

(52) U.S. Cl.
USPC ..... Plt./291
CPC ..... *A01H 6/1424* (2018.05)

(58) Field of Classification Search
USPC ..... Plt./291
See application file for complete search history.

*Primary Examiner* — Annette H Para
(74) *Attorney, Agent, or Firm* — C. Anne Whealy

(57) ABSTRACT

A new and distinct cultivar of *Chrysanthemum* plant named 'DLFPASC7', characterized by its upright plant habit; uniform growth habit; dark green-colored leaves; uniform and freely flowering habit; strong upright flowering stems; decorative-type inflorescences with deep purplish red-colored ray florets; relative tolerance to low temperatures; and excellent postproduction longevity.

2 Drawing Sheets

Figure 1:
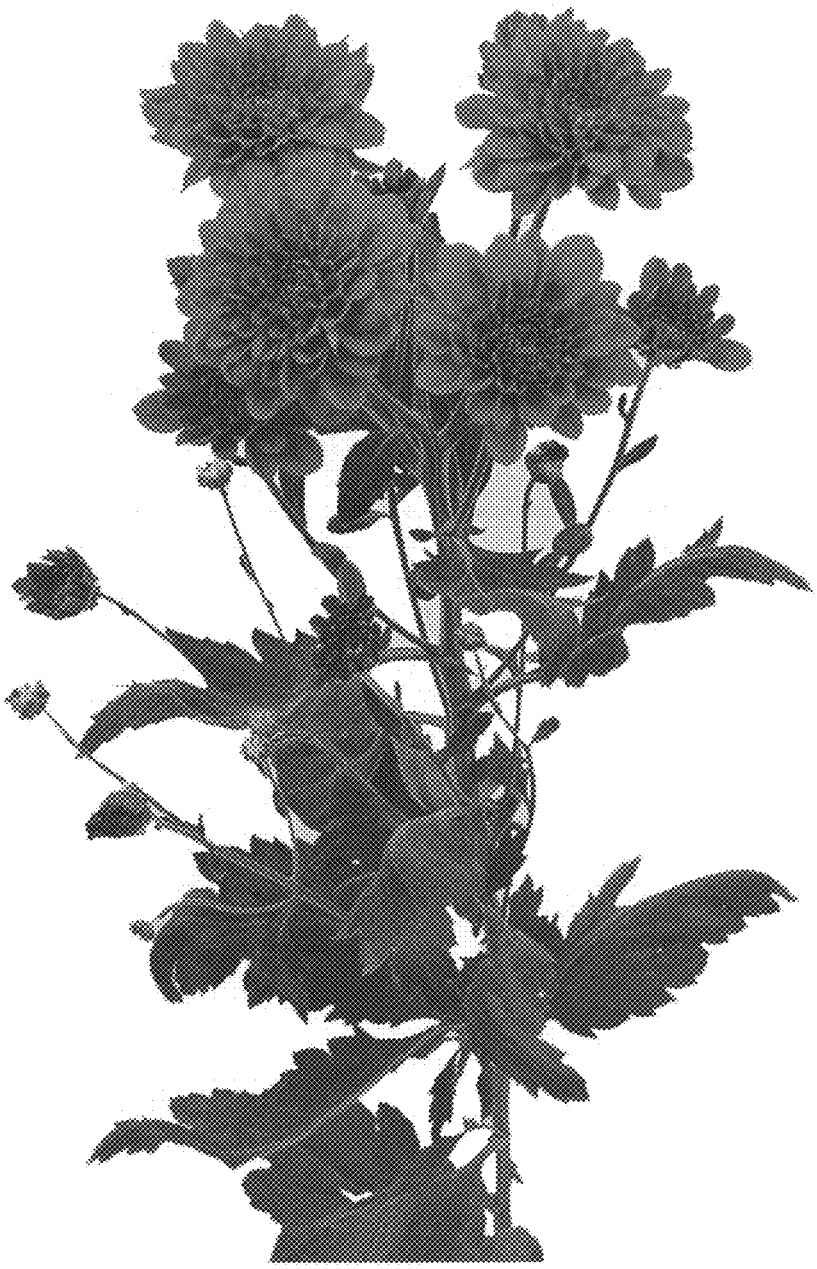

Botanical designation: *Chrysanthemum* X *morifolium*.
Cultivar denomination: 'DLFPASC7'.

STATEMENT REGARDING PRIOR DISCLOSURES BY INVENTOR/APPLICANT & ASSIGNEE

A Columbian Plant Breeder's Rights application for the instant plant was filed by the Assignee, Deliflor Royalties B.V. of Maasdijk, The Netherlands on May 26, 2020, application number A202658. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFPASC7'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in October, 2013 of a proprietary selection of *Chrysanthemum* x *morifolium* identified as code number db 33592, not patented, as the female, or seed, parent with a proprietary selection of *Chrysanthemum* x *morifolium* identified as code number db 42758, not patented, as the male, or pollen, parent. The new *Chrysanthemum* plant was discovered and selected as a single flowering plant from within the progeny of the stated cross-pollination in a controlled greenhouse environment in Maasdijk, The Netherlands in August, 2015.

Asexual reproduction of the new *Chrysanthemum* plant by vegetative terminal cuttings since August, 2015 in a controlled greenhouse environment in Maasdijk has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFPASC7'. These characteristics in combination distinguish 'DLFPASC7' as a new and distinct *Chrysanthemum* plant:

1. Upright plant habit; uniform growth habit.
2. Dark green-colored leaves.
3. Uniform and freely flowering habit.
4. Strong upright flowering stems.

5. Decorative-type inflorescences with deep purplish red-colored ray florets.
6. Relatively tolerant to low temperatures.
7. Excellent postproduction longevity.

Plants of the new *Chrysanthemum* differ primarily from plants of the female parent selection in ray floret color as ray florets of plants of the new *Chrysanthemum* are deep purplish red in color whereas ray florets of plants of the female parent selection are very pale purple in color. In addition, ray florets of plants of the new *Chrysanthemum* have obtuse to emarginate apices whereas ray florets of plants of the female parent selection have pointed apices.

Plants of the new *Chrysanthemum* differ primarily from plants of the male parent selection in ray floret color as ray florets of plants of the new *Chrysanthemum* are deep purplish red in color whereas ray florets of plants of the male parent selection are deep red in color.

Plants of the new *Chrysanthemum* can be compared to plants of *Chrysanthemum* X *morifolium* 'Barca', not patented. In side-by-side comparisons, plants of the new *Chrysanthemum* differ primarily from plants of 'Barca' in ray floret color as ray florets of plants of the new *Chrysanthemum* are deep purplish red in color whereas ray florets of plants of 'Barca' are dark greyed purple in color. In addition, ray florets of plants of the new *Chrysanthemum* are straight whereas ray florets of plants of 'Barca' are incurved.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) comprises a side perspective view of a typical flowering stem of 'DLFPASC7' grown as a spray-type cut flower.

Figure 2:
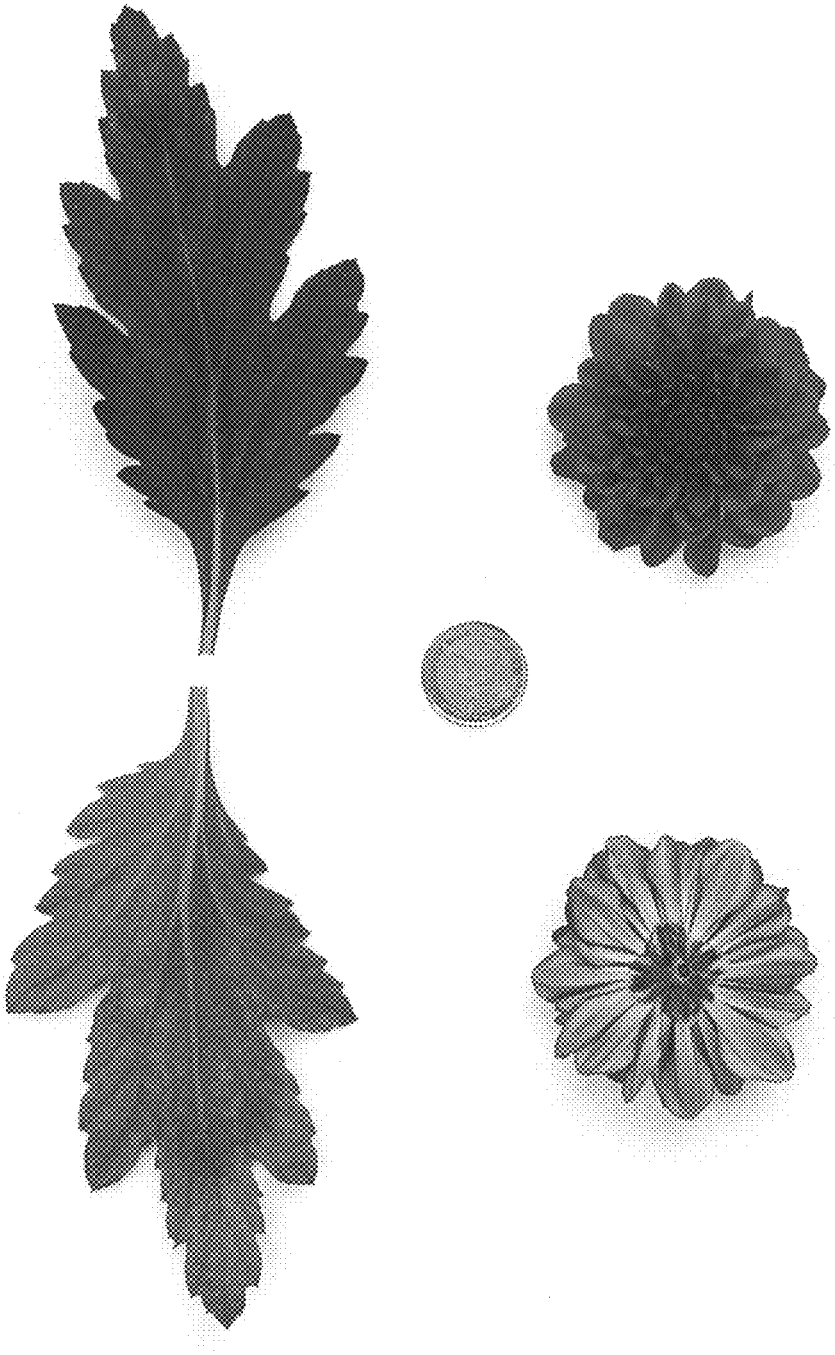

The photograph on the second sheet (FIG. 2) is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFPASC7'.

Parentage:

*Female, or seed, parent.*—Proprietary selection of *Chrysanthemum* x *morifolium* identified as code number db 33592, not patented.

*Male, or pollen, parent.*—Proprietary selection of *Chrysanthemum* x *morifolium* identified as code number db 42758, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About 13 days at temperatures about 20° C.

*Time to produce a rooted young plant, winter.*—About 15 days at temperatures about 20° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous decorative-type cut flower that is typically grown as a single stem spray-type; upright plant habit; vigorous growth habit and rapid growth rate.

*Plant height, soil level to top of foliar plane.*—About 76.3 cm.

*Plant height, soil level to top of inflorescence plane.*—About 84.5 cm.

*Plant (spray) diameter.*—About 21.4 cm.

*Flowering stem length.*—About 69.3 cm.

*Flowering stem diameter.*—About 7 mm.

*Flowering stem internode length.*—About 2.1 cm.

*Flowering stem strength.*—Strong.

*Flowering stem aspect.*—Erect.

*Flowering stem texture and luster.*—Densely pubescent; slightly glossy.

*Flowering stem color, developing.*—Close to 144B.

*Flowering stem color, developed.*—Close to 138A to 138B.

*Leaf description.*—Arrangement: Alternate; simple. Length: About 13.6 cm. Width: About 7.6 cm. Shape, in outline: Ovate to oblong. Apex: Abruptly acute, minute. Base: Attenuate. Margin: Palmately lobed, serrate to dentate; sinuses parallel to divergent and medium in depth. Texture and luster, upper surface: Moderately to densely pubescent, not rugose; moderately velvety; slightly glossy. Texture and luster, lower surface: Densely pubescent, prominent venation; slightly velvety; very slightly glossy. Venation pattern: Pinnate, reticulate. Color: Developing leaves, upper surface: Close to 137B. Developing leaves, lower surface: Close to 138B. Fully developed leaves, upper surface: Darker than NN137A; venation, close to 146B. Fully developed leaves, lower surface: Close to 147B; venation, close to 146B. Petioles: Length: About 1.7 cm. Diameter: About 3 mm by 4 mm. Strength: Moderately strong. Texture and luster, upper surface: Moderately pubescent; moderately glossy. Texture and luster, lower surface: Densely pubescent; moderately glossy. Color, upper surface: Close to 147C; edges, close to NN137A. Color, lower surface: Close to 146C; edges, close to 147A. Stipules: Quantity and appearance: Two leafy stipules, opposite, at the petiole attachment to the stem. Length: About 7 mm. Width: About 0.6 mm. Shape, in outline: Ovate to obovate;

occasionally cleft. Texture and luster, upper surface: Moderately to densely pubescent; slightly glossy. Texture and luster, lower surface: Densely pubescent; very slightly glossy. Color: Upper surface: Darker than NN137A; venation, close to 146B. Lower surface: Close to 147B; venation, close to 146B.

Inflorescence description:

*Appearance.*—Decorative-type inflorescence form with straight obovate to narrowly obovate-shaped ray florets and tubular disc florets; inflorescences borne perpendicular to peduncles and face upright; ray and disc florets develop acropetally on a capitulum.

*Fragrance.*—Faintly fragrant; typical of *Chrysanthemums.*

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 52 days later when grown as a spray-type.

*Postproduction longevity.*—Good postproduction longevity; after a seven-day storage period, cut flowers will maintain good color and substance for about two to three weeks in an interior environment; inflorescences persistent.

*Quantity of inflorescences.*—Typically grown as a spray-type, about 16 inflorescences develop per flowering stem.

*Inflorescence size.*—Diameter, grown as a spray-type: About 6.9 cm. Depth (height), grown as a spray-type: About 2.5 cm. Disc diameter: About 6 mm.

*Receptacles.*—Height: About 4 mm. Diameter: About 7 mm. Shape: Flattened globular. Color: Close to 145B.

*Inflorescence buds.*—Height: About 1.3 cm. Diameter: About 1.5 cm. Shape: Flattened globular to roughly globular. Texture and luster: Distally, smooth and glabrous; proximally, densely pubescent; moderately glossy. Color: Close to NN137B, 138A and 138B; immature ray florets, close to 71A.

*Ray florets.*—Quantity and arrangement: About 200 arranged in about five whorls. Length: About 2.4 cm, varying between 1 cm and 3.3 cm. Width: About 1 cm, varying between 0.2 cm and 1.5 cm. Shape: Obovate to narrowly obovate; straight. Apex: Obtuse to shallowly emarginate. Base: Attenuate. Margin: Entire; not undulate. Aspect: About 20° to 70° from vertical. Texture and luster, upper surface: Smooth, glabrous; velvety; matte. Texture and luster, lower surface: Smooth, glabrous; slightly velvety; very slightly glossy. Color: When opening, upper surface: Close to 59A. When opening, lower surface: Close to 64A. Fully opened, upper surface: More intense than close to between 61A and 71A; venation, similar to lamina colors; color becoming closer to 72A with development. Fully opened, lower surface: Close to N74D and 75A to 75C; venation, similar to lamina colors; color does not change with development.

*Disc florets.*—Quantity and arrangement: About 50 at the center of the receptacle. Length: About 6 mm. Diameter: About 1 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Close to 145D; towards the apex, close to N144A to N144B. Color, fully opened, inner and outer surfaces: Close to 145D; towards the apex, close to N144B.

*Involucral bracts.*—Quantity and arrangement: About 24 arranged in about two whorls. Length: About 1 cm. Width: About 5 mm. Shape: Ovate to narrowly ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Close to 143A; lateral margins, translucent and close to 157D and apical margins tinged with close to N199A. Color, lower surface: Close to NN137B; lateral margins, translucent and close to 157D and apical margins tinged with close to N199A.

*Peduncles.*—Length, terminal peduncle: About 10.3 cm. Diameter, terminal peduncle: About 3 mm. Length, third peduncle: About 13.5 cm. Diameter, third peduncle: About 3 mm. Strength: Strong. Aspect, terminal peduncle: Upright. Aspect, third peduncle: About 30° from the flowering stem axis. Texture and luster: Densely pubescent; moderately glossy. Color: Close to 138A.

*Reproductive organs.*—Androecium: Present on disc florets only. Quantity: About five per floret. Filament length: About 2 mm. Filament color: Close to 145D. Anther size: About 0.5 mm by 1.5 mm. Anther shape: Narrowly oblong. Anther color: Close to 154D. Pollen amount: Moderate. Pollen color: Close to 14A. Gynoecium: Present on both ray and disc florets. Quantity: One per floret. Pistil length: About 7 mm. Style length: About 6.5 mm. Style color: Close to 145D. Stigma diameter: About 1 mm. Stigma shape: Cleft, decurrent. Stigma color: Close to 153D. Ovary color: Close to 157A.

*Seeds and fruits.*—To date, seed and fruit production have not been observed on plants of the new *Chrysanthemum.*

Pathogen & pest resistance: To date, plants of the new *Chrysanthemum* have not been observed to be resistant to pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFPASC7' as illustrated and described.

* * * * *